United States Patent
Yang

(10) Patent No.: US 6,855,720 B2
(45) Date of Patent: Feb. 15, 2005

(54) NITROGEN-BASED CAMPTOTHECIN DERIVATIVES

(75) Inventor: Li-Xi Yang, San Francisco, CA (US)

(73) Assignees: California Pacific Medical Center, San Francisco, CA (US); Catholic Healthcare West, S.F., CA (US)

(*) Notice: Subject to any disclaimer, the term of this patent is extended or adjusted under 35 U.S.C. 154(b) by 0 days.

(21) Appl. No.: 10/172,211

(22) Filed: Jun. 14, 2002

(65) Prior Publication Data

US 2003/0032624 A1 Feb. 13, 2003

Related U.S. Application Data

(63) Continuation-in-part of application No. 10/154,768, filed on May 23, 2002, which is a continuation of application No. 09/797,765, filed on Mar. 1, 2001, now Pat. No. 6,403,604.

(51) Int. Cl.[7] ............................ A61K 31/44; C07F 7/02; C07D 491/22
(52) U.S. Cl. .............................. 514/283; 546/14; 546/48
(58) Field of Search ............................ 514/283; 546/14, 546/48

(56) References Cited

U.S. PATENT DOCUMENTS

| | | | |
|---|---|---|---|
| 4,399,282 A | 8/1983 | Miyasaka et al. | |
| 4,943,579 A | 7/1990 | Vishnuvajjala et al. | |
| 5,916,896 A | 6/1999 | Wall et al. | |
| 5,965,566 A | 10/1999 | Greenwald et al. | |
| 6,028,078 A | 2/2000 | Hausheer et al. | |
| 6,040,313 A | 3/2000 | Wall et al. | |
| 6,057,303 A | 5/2000 | Haridas et al. | |
| 6,096,336 A | 8/2000 | Cao et al. | |
| 6,113,906 A | 9/2000 | Greenwald et al. | |
| 6,114,529 A | 9/2000 | Kawaguchi et al. | |
| 6,120,793 A | 9/2000 | Cao et al. | |
| 6,127,355 A | 10/2000 | Greenwald et al. | |
| 6,153,655 A | 11/2000 | Martinez et al. | |
| 6,207,832 B1 | 3/2001 | Curran et al. | |
| 6,339,091 B1 | 1/2002 | Bigg et al. | |
| 6,350,756 B1 | 2/2002 | Yang et al. | |
| 6,403,604 B1 * | 6/2002 | Yang et al. | 514/283 |

FOREIGN PATENT DOCUMENTS

| | | |
|---|---|---|
| EP | 0 861 842 A | 9/1998 |
| WO | WO 95/10304 A1 | 4/1995 |
| WO | WO 96/26950 A1 | 9/1996 |
| WO | WO 97/19085 A1 | 5/1997 |
| WO | WO 97/28165 A1 | 8/1997 |
| WO | WO 98/13059 A1 | 4/1998 |
| WO | WO 98/14459 A1 | 4/1998 |
| WO | WO 98/28304 A1 | 7/1998 |
| WO | WO 98/35940 A1 | 8/1998 |
| WO | WO 98/51703 A1 | 11/1998 |
| WO | WO 99/17805 A1 | 4/1999 |
| WO | WO 00/66127 A1 | 11/2000 |
| WO | WO 00/67801 A2 | 11/2000 |
| WO | WO 03/014069 A1 | 2/2003 |

OTHER PUBLICATIONS

Stein, J., Editor–in–Chief, Internal Medicine, 4th Edition, Chapters 71 and 72, 1994.*

Bom, David et al., "The Novel Silatecan 7–tert–Butyldimethylsilyl–10–hydroxycamptothecin Displays High Lipophilicity, Improved Human Blood Stability, and Potent Anticancer Activity," J. Med. Chem., 2000, v. 43, pp. 3970–3980.

Cao, Zhisong et al., "Alkyl Esters of Camptothecin and 9–Nitrocamptothecin: Synthesis, in Vitro Pharmacokinetics, Toxicity, and Antitumor Activity," J. Med. Chem., 1998, v. 41, pp. 31–37.

Dallavalle, Sabrina et al., "Novel 7–Substituted Camptothecins with Potent Antitumor Acitvity," J. Med Chem., 2000, v. 43, pp. 3963–3969.

Del Poeta, Maurizio et al., "Comparison of In Vitro Activities of Camptothecin and Nitidine Derivatives against Fungal and Cancer Cells," Antimicrobial Agents and Chemotherapy, Dec. 1999, v. 43, n. 12, pp. 2862–2868.

Keskin et al., Anti–Cancer Drug Des. (2000), 15(2):79–98 Abstract.

Kingsbury, William D. et al., "Synthesis of Water–Soluble (Aminoalkyl)camptothecin Analogues: Inhibition of Topoisomerase I and Antitumor Activity," J. Med. Chem., 1991, v. 34, pp. 98–107.

O'Leary, J. et al., "Camptohecins: a Review of their Development and Schedules of Administration," European Journal of Cancer, 1998 v. 34, n. 10, pp. 1500–1508.

Saltz L. et al., "CPT–11 (Irinotecan) and 5–Fluorouracil: a Promising Combination for Therapy of Colorectal Cancer", European Journal of Cancer, 1996, vol. 32A, No. Suppl. 3, pp. 524–531.

Singer et al., "Conjugation of Camptothecins to Poly–(L–Glutamic Acid)", Annals of the New York Academy of Sciences, 2000, vol. 922, pp. 136–150.

Sawada, Seigo et al., "Chemical Modification of an Antitumor Alkaloid Camptothecin: Synthesis and Antitumor Acitivity of 7–C–Substituted Camptothecins," Chem. Pharm. Bull., 1991, v. 39, n. 10, pp. 2574–2580.

Sawada, Seigo et al., "Synthesis and Antitumor Activity of 20(S)–Camptothecin Derivatives: Carbamate–Linked, Water–Soluble Derivatives of 7–Ethyl–10–hydroxycampto thecin," Chem. Pharm. Bull., 1991, v. 39, n. 6, pp. 1446–1454.

(List continued on next page.)

*Primary Examiner*—Dwayne Jones
(74) *Attorney, Agent, or Firm*—Cooley Godward LLP

(57) ABSTRACT

(20S) esters of camptothecin analogs are provided. The compounds are (20S) esters of an aminoalkanoic acid or an imidoalkanoic acid and camptothecin, which is optionally substituted at the 7, 9, 10, 11, and 12 positions of the camptothecin ring. The compounds are useful for treating cancer.

29 Claims, No Drawings

OTHER PUBLICATIONS

Takayama, Hiromitsu et al., "Synthesis of a New Class of Camptothecin Derivatives, the Long–Chain Fatty Acid Esters Of 10–Hydroxycamptothecin, as a Potent Prodrug Candidate, and their In Vitro Metabolic Conversion by Carboxylesterases," Bioorganic & Medicinal Chemistry Letters 8, 1998, pp. 415–418.

Wall, Monroe E. et al., "Camptothecin and Taxol: Discovery to Clinic—Thirteenth Bruce F. Cain Memorial Award Lecture," Cancer Research 55, Feb. 15, 1995, pp. 753–760.

Wall, Monroe E. et al., "Plant Antitumor Agents. $30.^{lab}$ Synthesis and Structure Activity of Novel Camptothecin Analogs," J. Med. Chem., 1993, v. 36, pp. 2689–2700.

Zhao, Rulin et al., "Synthesis, topoisomerase I inhibitory activity and in vitro cytotoxicity of camptothecin derivatives bearing five–membered heterocycle containing 10–substituents," Anti–Cancer Drug Design, 1998, v. 13, pp. 145–157.

XP 002033248, Abstract, WPI, vol. 46, No. 89.

XP 002033250 Abstract, WPI, vol. 45, No. 89.

Bomgaars, et al., "The Development of Camptothecin Analogs in Childhood Cancers," Oncolgist 6:506–516 (2001).

Lerchen, "Milestones in Camptothecin Research," Drugs of the Future 27:869–876 (2002).

Garcia–Carbonero et al., "Current Perspectives on the Clinical Experience, Pharmacology and Continued Development of the Camptothecins", *Clinical Cancer Research*, Mar. 2002, vol. 8, 641–661.

Shabat D et al., "Multiple event activation of a generic prodrug trigger by antibody catalysis", Proceedings of the National Academy of Sciences of USA, 96:6925–6930, Jun. 1999.

Keskin, O. et al., "Characterization of anticancer agents by their growth inhibitory activity and relationships to mechanism of action and structure", Anti Cancer Drug Design, 15:2:78–98 (2000).

Maliepaard et al., "Circumvention of breast cancer resistance protein (BCRP)–mediated resistance to camptothecins in vitro using non–substrate drugs or the BCRP inhibitor GF120918," *Clinical Cancer Research* 7:935–941, 2001.

Nomoto et al., "Characterization of a human small–cell lung cancer cell line resistant to a new water–soluble camptothecin derivative, DX–8951f," *Jpn. J. Cancer Res.* 89:1179–1186, 1998.

Perego et al., "A novel 7–modified camptothecin analog overcomes breast cancer resistance protein–associated resistance in a mitoxantrone–selected colon carcinoma cell line," *Cancer Research* 61:6034–6037, 2001.

Pollack et al., "Potent topoisomerase I inhibition by novel silatecans eliminates glioma proliferation in vitro and in vivo," Cancer Research 59:4898–4905, 1999.

\* cited by examiner

NITROGEN-BASED CAMPTOTHECIN DERIVATIVES

CROSS-REFERENCE TO RELATED APPLICATION

This application is a continuation-in-part of U.S. patent application Ser. No. 10/154,768, filed May 23, 2002, which in turn is a continuation Application of U.S. patent application Ser. No. 09/797,765 filed Mar. 1, 2001 now U.S. Pat. No. 6,403,604. The entire content of both applications is incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of contract number DAMD 1-99-9018 awarded by the Department of Defense.

FIELD OF THE INVENTION

This invention relates to novel camptothecin derivatives that are useful for treating various types of cancer.

BACKGROUND OF THE INVENTION

Camptothecin (often abbreviated as "CPT"), a phytotoxic alkaloid first isolated from the wood and bark of *Camptotheca acuminata* (Nyssaceae) by Wall and coworkers in 1966, was shown to have antitumor activity against the mouse leukemia L1210 system. The compound has a pentacyclic ring system with an asymmetric center in ring E with a 20 S configuration. The pentacyclic ring system includes a pyrrolo [3,4-b] quinoline (rings A, B and C), a conjugated pyridone ring D), and six membered lactone (ring E) with an 20S-hydroxyl group. Camptothecin itself is essentially insoluble in water. Therefore, camptothecin was evaluated clinically as a water soluble sodium carboxylate salt in the early stages. It appears that the carboxylate salt was actually the compound where the E ring was open to form the sodium salt. This sodium salt produced severe toxicity and had very little anticancer activity. Thus early work on camptothecin was discontinued after starting phase II trials. However, interest in the compound revived when it was found to inhibit topoisomerase, an enzyme that is required for its swiveling and relaxation of DNA during molecular events such as replication and transcription. A number of syntheses and modifications of the molecule have been reported in the literature and new derivatives have been prepared over the years. For example, topotecan (9-dimethylaminomethyl-10-hydroxy CPT) and irinotecan (7-ethyl-10[4-(1-piperidino)-1-piperidino] carbonyloxy CPT) show clinical useful activity. This invention defines a new series of 20 S esters that are useful for treating various types of cancer. The novel compounds have higher potency and lower toxicity than CPT and other CPT derivatives.

SUMMARY OF THE INVENTION

One aspect of this invention is a compound of the formula (I), below,

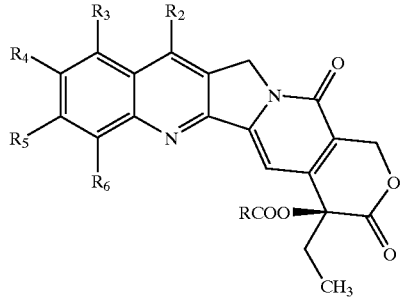

wherein R is $R_a R_b N(CH_2)_m$, m is an integer of 1–10 (preferably 2), and each of $R_a$ and $R_b$ is independently lower alkyl substituted with one to five substituents independently selected from the group consisting of halo, lower alkoxy, hydroxy, cyano, nitro, or amino;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperidino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

lower alkoxy; or $R_a R_b$ together with N form a cyclic amine or imide ring;

$R_2$ is hydrogen, halo, lower alkyl, lower alkoxy, hydroxy, RC(O)O(R defined hereinbefore), cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonylmethyl, benzoylmethyl, benzylcarbonyloxymethyl, —$CH_2NR_7R_8$ (where $R_7$ and $R_8$ taken together with —$N_2$ represent a cyclic amino), or mono- or di lower alkoxymethyl, or $R_2$.taken together with $R_3$ is —$CH(NR_{12}R_{13})$—CH2—CH2— (where $R_{12}$ and $R_{13}$ each is independently hydrogen or lower alkyl).

$R_3$ is hydrogen, halo, lower alkyl, lower alkoxy, hydroxy, RC(O)O(R defined hereinbefore) cyano, nitro, amino, halogenated lower alkyl, halogenated lower alkoxy, hydroxycarbonyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$, taken together with —N— represent a cyclic amino), dialkylamino alkyl, lower alkylcarbonyloxy, lower alkylcarbonylamino, or trialkylsilylethylene;

$R_4$ is hydrogen, halo, lower alkyl, lower alkoxy, hydroxy, RC(O)O (R defined hereinbefore) cyano, nitro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or $R_4$ together with $R_5$ is methylenedioxy;

$R_5$ is hydrogen, halo, lower alkyl, lower alkoxy, hydroxy, RC(O)O(R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino, or $R_5$ together with $R_4$ is methylenedioxy or ethylenedioxy; and $R_6$ is hydrogen, halo, lower alkyl, lower alkoxy, hydroxy, RC(O)O(R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino.

Another aspect of the invention is a pharmaceutical composition useful for treating cancer in a warm-blooded animal, which composition comprises compound of the invention as defined herein in combination with a pharmaceutically acceptable excipient.

Another aspect of this invention is a method for treating cancer in a warm-blooded animal, which method comprises administering a therapeutically effective amount of a compound of the invention as defined herein. The compound, is administered in a therapeutically effective dose by appropriate administration, e.g. orally, topically, or parenterally.

Another aspect of this invention is process for preparing compounds of this invention by reacting camptothecin (CPT) or a CPT analog with a compound of the formula R—C(O)X, wherein R is $R_aR_bN(CH_2)_2$, where $R_a$ and $R_b$ are as defined herein, and X is e.g. bromide, chloride, hydroxy, alkoxy of 1–11 carbons.

Still another aspect of this invention is a liposomal formulation of a compound of this invention.

Other aspects of this invention will be apparent to one of skill in the art by reviewing the ensuing specification.

DETAILED DESCRIPTION

Overview

In general this invention can be viewed as a (20S) ester of CPT or a CPT analog. As noted hereinbefore CPT is the (S) stereoisomer having a hydroxy at the 20 position. This hydroxy group is esterified in accordance with the process of this invention to form the corresponding (20S) ester in a stereospecific conversion in good yield. The resulting ester is unique in that has an electronegative entity in the chain, which is believed to aid in stabilizing the E ring of the camptothecin molecule. The novel compounds of the invention are active against tumors in mice and are generally well tolerated. They are useful for treating various types of cancer and can be formulated to prepare pharmaceutical preparations, e.g. for oral, topical, or parenteral administation.

While not wishing to be bound by any particular mechanism of action or theoretical explanation of how the compounds work, it is believed that the 20S esters exert their effect in part by stabilizing the E ring of the CPT molecule. The esters may accomplish this through steric hinderance by preventing enzymatic access to the E ring, through the presence of an electron-withdrawing group in the ester chain, i.e. a nitrogen atom, and through facilitating the hydrogen-binding or Van Der Walls forces of the E ring end of the CPT molecule with the enzyme to inhibit binding and thus enzyme activity to sever the E ring.

Definitions

The term "CPT" is an abbreviation for camptothecin, also known as (S)-4-ethyl-4-hydroxy-1H-pyrano-[3',4':6,7] indolizinol[1,2-b]quinoline-3,14(4H, 12H)-dione. The compound is readily available from numerous sources, e.g., Sigma Chemical Co., St. Louis, Mo. The chemical formula of camptothecin and its numbering system are as follows:

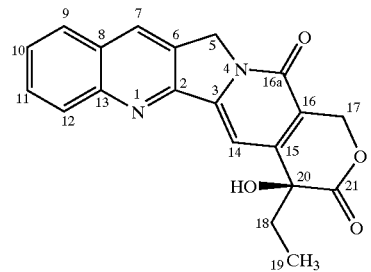

The compound has a hydroxy at the 20-position that is esterified to make the compounds of this invention.

The term "alkyl" refers to a monovalent, saturated aliphatic hydrocarbon radical having the indicated number of carbon atoms. For example, a "C1–6 alkyl" or an "alkyl of 1–6 carbons" or "Alk1–6" would refer to any alkyl group containing one to six carbons in the structure. "C1–20 alkyl" refers to any alkyl group having one to twenty carbons. Alkyl may be a straight chain (i.e. linear) or a branched chain. Lower alkyl refers to an alkyl of 1–6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The term "alkoxy" refers to a monovalent radical of the formula RO—, where R is an alkyl as defined herein. Lower alkoxy refers to an alkoxy of 1–6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The radical may be optionally substituted with one to five substituents independently selected from the group consisting of halo, lower alkyl, lower alkoxy, hydroxy, cyano, nitro, or amino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovolent radical having the formula —C(O)OH.

The term "lower alkoxycarbonyl" is a monovalent radical having the formula —C(O)OAlk, where Alk is lower alkyl.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

A "halo" substitutent is a monovalent halogen radical chosen from chloro, bromo, iodo, and fluoro. A "halogenated" compound is one substituted with one or more halo sustituent.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino.

A "carbamoyloxy" is a monovalent radical of the formula $R_{13}R_{14}NC(O)O—$ (i.e. an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others delineated herein.

A "5-membered heterocyclic ring" is a monovalent radical of a 5-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The heterocyclic radical is bonded through an available carbon atom in the heteocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "6-membered heterocyclic ring" is a monovalent radical of a 6-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 6-membered heterocycles with only one hetero atom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g. 2-piperazine. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "cyclic amino" is a monovalent radical of a saturated 5-, 6-, or 7-membered cyclic amine ring having no more than one additional hetero atom such as nitrogen, oxygen, or sulfur, or a 5-, 6-, or 7-membered cyclic amine fused to another, carbocyclic ring or rings. Representative examples include, e.g., 1-pyrrolidino, 1-piperidino, morpholino, piperazino, 3-benzopiperidino, and the like. These may be substituted or unsubstituted. If substituted, generally they will have no more than 2 substituents chosen from lower alkyl, lower cycloalkyl, hydroxy lower alkyl, phenyl (substituted or unsubstituted), benyzl (substituted or unsubstituted), aminocarbonylmethyl, lower alkylaminocarbonylmethyl, amino, mono-or di-lower alkylamino, cyclic amino, or a 5- or 6-membered heterocyclic ring.

An "imide ring" is a cyclic imide wherein the nitrogen of the cyclic structure is bonded on each side to a carbonyl group, which in turn is bound to carbon atoms to form a ring. An imide ring would include, e.g. phthalimide (which may be substituted on the benzene ring) maleimide, 1,8-naphthalimide (which may be substituted on the naphthyl ring—e.g 3-nitro-1,8-naphthalimide, 4-nitronaphalimide, 4-bromo-napthalimide, and the like). Others will be apparent to one of skill in the art.

Other chemical terms are given their standard meaning as understood by one of skill in the art with guidance from standard texts and dictionaries.

The term "MTD" is the abbreviation for maximum tolerated does.

The term "nM" is the abbreviation for nanomolar.

The term "ip" is the abbreviation for intraperitonial.

Compounds of the Invention

One aspect of this invention is a compound of the formula

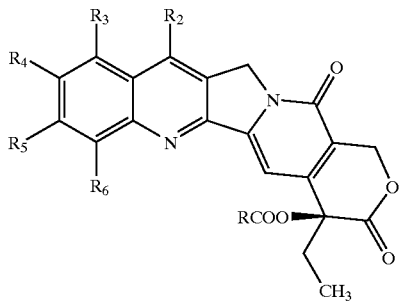

wherein R is $R_aR_bN$—$(CH_2)_m$, m is an integer of 1–10 (preferably 2), and each of $R_a$ and $R_b$ is independently lower alkyl substituted with one to five substituents independently selected from the group consisting of halo, lower alkoxy, hydroxy, cyano, nitro, or amino;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkyl carbonyloxy, benzyloxy, optionally substituted piperidino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

lower alkoxy; or $R_aR_b$ together with N form a cyclic amine or imide ring;

$R_2$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonylmetbyl, benzoylmethyl, benzylcarbonyloxymethyl, or mono- or di lower alkoxymethyl;

$R_3$ is hydrogen, halo, lower alkyl, lower alkoxy, hydroxy, RC(O)O(R defined hereinbefore) cyano, nitro, amino, halogenated lower alkyl, halogenated lower alkoxy, hydroxycarbonyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2$ $R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, lower alkylcarbonylamino, or trialkylsilylethylene;

$R_4$ is hydrogen, halo, lower alkyl, lower alkoxy, hydroxy, RC(O)O (R defined hereinbefore) cyano, intro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or $R_4$ together with $R_5$ is methylenedioxy;

$R_5$ is hydrogen, halo, lower alkyl, lower alkoxy, hydroxy, RC(O)O(R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino, or $R_5$ together with $R_4$ is methylenedioxy or ethylenedioxy; and $R_6$ is hydrogen, halo, lower alkyl, lower alkoxy, hydroxy, RC(O)O(R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino.

A preferred aspect is a compound of formula (I) wherein each $R_2$ through $R_6$ is H (or the preferences given hereinafter), m is 2, and $R_aR_bN$ is a cyclic amino or cyclic imido radical.

Another preferred aspect is a compound of formula (I) wherein each $R_2$ through $R_6$ is H (or the preferences given hereinafter), m is 2, and $R_aR_bNCH_2$—$CH_2$ is one of the following cyclic amino ethyl or cyclic imido ethyl radicals:

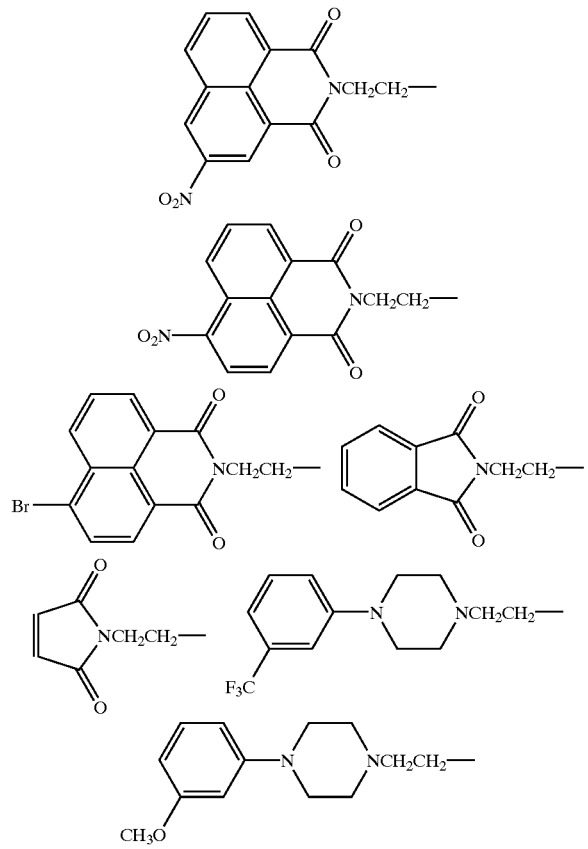

-continued

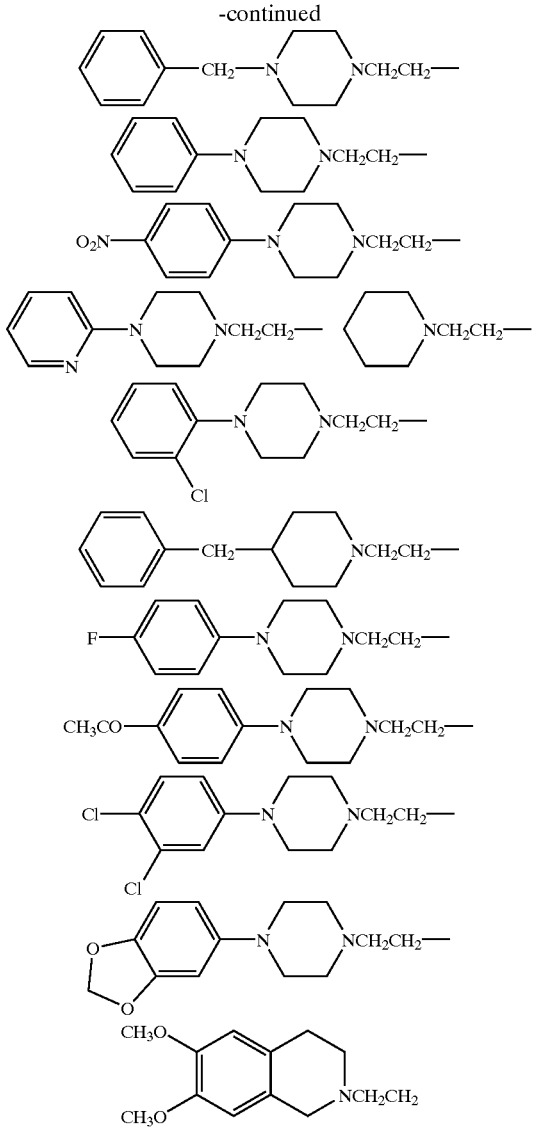

Other aspects of the invention include compounds as described hereinbefore, but where $R_2$, $R_3$, $R_4$, $R_5$, and $R_6$ each may be a substituent other than only hydrogen. These include, for example, the preferred subgroups set forth hereinafter:

The compound of formula (I), wherein $R_6$ is hydrogen, particularly a compound wherein $R_4$ and $R_5$ together are methylenedioxy and wherein $R_2$ is hydrogen. Of these the compounds particular interest are those where $R_3$ is nitro, amino, methyl, chloro, cyano, acetoxy, or acetylamino.

A compound of formula (I), wherein each of $R_5$ and $R_6$ is hydrogen, especially those wherein $R_3$ is hydrogen; $R_2$ is (3-chloro-n-propyl)dimethylsilyl, tert-butyldimethylsilyl, acetoxymethyl, cyano, formylethenyl, ethoxycarbonyl-ethenyl, cyanoethenyl, 2,2-dicyanoethenyl, (2-cyano-2-ethoxycarbony)ethenyl, ethoxycarbonylethyl, methyl, ethyl, or n-propyl; and $R_4$ is hydroxy, acetoxy, amino, nitro, cyano, chloro, bromo, fluoro, lower alkyl, higher alkyl, lower alkoxy, carbamoyloxy, or formyl. Of these, the compounds wherein $R_2$ is ethyl and $R_4$ is carbamoyloxy are of further interest. Carbamoyloxy substituents that are preferred include 1-pyrazinylcarbonyloxy, 4-(i-propylaminocarbonylmethyl)-1-pyrazinyl-carbonyloxy, or [4-(1-piperidio)-1-piperidinocarbonyloxy.

The compound of formula (I), wherein each of $R_2$, $R_5$, and $R_6$ is hydrogen, for example, those wherein $R_3$ is amino, nitro, cyano, halo, OH, lower alkylamino, di-lower alkylamino, lower alkyl, lower alkoxy, 1-piperidino, 1-mopholino, aminomethyl, lower alkylaminomethyl, cycloalkylaminomethyl, di-lower alkylaminomethyl, cyclic aminomethyl, acetoxy, acetylamino, lower alkoxymethyl, omega hydroxy lower alkylaminomethyl, cyanomethyl and $R_4$ is hydroxy, acetoxy, cyano, nitro, amino, halo, formyl, lower alkoxy, carbamoyloxy.

A compound wherein each of $R_2$, $R_3$, $R_5$ and $R_6$ is hydrogen and $R_4$ is —OC(O)Alkyl$_{1-20}$.

Other compounds of interest include the following:
—$R_3$ and $R_6$ are H, $R_2$ is 4-methylpiperazinomethylene, and $R_4$ and $R_5$ together are ethylenedioxy;

$R_2$ and $R_3$ together are —CH(NH$_2$)—CH$_2$—CH$_2$— (the CH$_2$— attached at 9 and —CH(NH$_2$) attached at 9), $R_4$ is methyl, $R_5$ is fluoro, and $R_6$ is —H;

each of $R_2$, $R_4$, $R_5$, and $R_6$ is —H and $R_3$ is trimethylsilylethylene; and each of $R_3$, $R_4$, $R_5$, and $R_6$ is —H and $R_2$ is butoxyiminomethyl.

Pharmaceutical Composition of the Invention

This aspect of the invention is a pharmaceutical composition useful for treating cancer in a warm-blooded animal, which composition comprises compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the 18$^{th}$ or 19$^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91–93 for a fuller discussion.

A compound may be administered parenterally, e.g., intravenously, intramuscularly, intravenously, subcutaneously, or interperitonieally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Although the compounds of this invention tend to be water soluble, in some cases, e.g., where a compound of the invention is less water soluble, it may be useful to provide liposomal delivery. The system restrains the compound of the invention by incorporating, encapsulating, surrounding, or entrapping the compound of the invention in, on, or by lipid vesicles or liposomes, or by micelles.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255–3261; Perex-Soler, et al., *Cancer Res.* 1990, 50: 4260–4266; and, Khokhar, et al., *J. Med. Chem.* 1991, 34: 325–329, all of which are incorporated herein in their entireties by reference.

Similarly, micelles have also been used to deliver medications to patients, (Broden et al., *Acta Pharm Suec.* 19: 267–284 (1982)) and micelles have been used as drug carriers and for targeted drug delivery, (D. D. Lasic, *Nature* 335: 279–280 (1992); and, Supersaxo et al., *Pharm Res.* 8: 1280–1291 (1991)), including cancer medications, (Fung et al., *Biomater. Artif. Cells. Artif. Organs* 16: 439 et seq. (1988); and Yokoyama et al., *Cancer Res.* 51: 3229–3236 (1991)), al of which are incorporated herein in their entireties by reference.

The liposomes and/or micelles containing the compound of the invention can be administered to a cancer patient, typically intravenously. Further guidance for preparing liposomal compositions useful in this invention may be found in U.S. Pat. No. 6,096,336, which is incorporated herein by reference.

Method of Treatment of the Invention

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W. B. Saunders Company). This information from Chapter 8 is incorporated herein by reference. The following Table A provides examples of the types of cancers, i.e., malignant tumors or neoplasia that may be treated by administering a compound of this invention.

TABLE A

| Tissue of Origin | Malignant |
| --- | --- |
| Composed of One Parenchymal Cell Type Mesenchymal tumors | |
| Connective tissue and derivatives | Fibrosarcoma |
| | Liposarcoma |
| | Chondrosarcome |
| | Osteogenic sarcoma |
| Endothelial and related tissues | |
| Blood vessels | Angiosarcoma |
| Lymph vessels | Lymphangiosarcoma |
| Synovium | Synovial sarcoma |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Straited | Rhabdomyosarcoma |
| Epthelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

The compounds of the invention are thus useful in the treatment of leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of CPT derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on $mg/m^2$ of body surface) is described by E. J. Freireichet al., *Cancer Chemother. Rep.*, 50(4):219 (1966). Body surface area may be approximately determined from the height and weight of an individual (see, e.g., Scientific Tables, Geigy Pharmaceuticals, Ardsley, N.Y. pp. 537–538 (1970)). A suitable dose range is from 1 to 1000 mg of equivalent per $m^2$ body surface area of a compound of the invention, for instance from 50 to 500 $mg/m^2$.

For all of the administering routes, the exact timing of administration of the dosages can be varied to achieve optimal results. Generally, if using Intralipid 20 as the carrier for the CPT derivative, the actual dosage of CPT derivative reaching the patient will be less. This is due to some loss of the CPT derivative on the walls of the syringes, needles and preparation vessels, which is prevalent with the Intralipid 20 suspension. When a carrier, such as cottonseed oil is used, this above described loss is not so prevalent because the CPT derivative does not adhere as much to the surface of syringes, etc.

Another important feature of the method provided by the present invention relates to the relatively low apparent overall toxicity of the CPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Process of the Invention

Another aspect of this invention is process for preparing compounds of this invention by reacting camptothecin (CPT) or a CPT analog with a compound of the formula R—C(O)X, wherein R is $R_aR_bN(CH_2)_m$, $R_a$ and $R_b$ are as defined herein, and X is e.g. bromide, chloride, hydroxy, alkoxy of 1–11 carbons (e.g —$O(CH_2)_n$ $CH_3$ where n is an integer of 1–10) or R—C(O)O—(R is defined hereinbefore). Preferably X is OH. The compound shown as $R_aR_bN(CH_2)_mC(O)X$ can be referred to as an aminoalkanoic acid or aminoalkanoic acid derivative, e.g. where m is 2, it is an "aminopropionic acid" or an "aminopropionic acid derivative." One way that such an aminoalkanic acid (e.g. aminopropionic acid) is obtained is by reacting an appropriate amino $R_aR_bNH$ or the imido $R_aR_bNH$ (or their acid addition salt) with an omega-halosubstituted alkanoic acid (e.g. 3-halopropionic ester), then hydrolyzing the ester to form the acid. Examples of preferred halopropionic esters include the ethyl ester of 3-bromopropionic acid, 3-chloropropionic acid, or 3-iodopropionic acid. Other corresponding alkyl esters (e.g., methyl, propyl, and the like, are useful but ethyl is preferred). The ethyl ester of 3-bromopropionic acid is preferred. In some cases, it may be useful to prepare an acid halide from the corresponding aminopropionic acid. The acid halides are obtained by reacting the corresponding aminopropionic acid with halogenated agents (such as $SOCl_2$, $PCl_3$, $POCl_3$, $PCl_5$, $PBr_3$, and so on). The acid chloride is preferred. Once the acid or its derivative is prepared, it is reacted with CPT to form the (S)-20-ester of CPT, i.e. compounds of this invention. This reaction sequence can be generalized as follows:

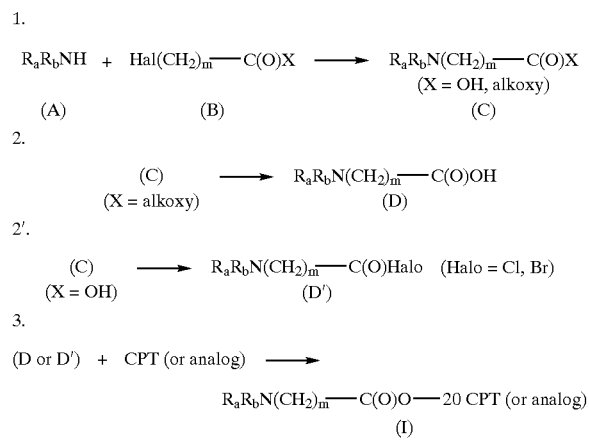

In step 1 the reaction conditions will vary depending on the exact reactants employed. In general, solvents useful in the reaction may be aqueous or nonaqueous. Preferably, a solvent will be a polar organic solvent miscible with water such as a lower alkanol (ethanol is preferred). Examples of other useful polar solvents include methanol, propanol, acetone, and dimethylformamide (DMF). The reaction will generally take place in the presence of an alkaline salt such as sodium bicarbonate. The reaction temperature will vary with the reactant, and the solvents, and will range from about 20° C. to about 180° C., preferably at reflux temperature until the free amine disappears, i.e., it is not detected anymore. The time needed for the reaction to be complete will generally be no more than about 20 hours, preferably no more than about 6 hours.

In step 2, the compound of formula (C) is converted to a compound of formula (D) by a hydrolysis reaction, generally performed in two stages. The reaction conditions for this step will vary in accordance with the compound being reacted. In general, solvents useful in the conversion may be aqueous, preferably, a solvent will be water, either alone or with a water-miscible organic solvent. An example of a particularly useful solvent is a mixture of water and dioxane. The pH of the first stage of reaction will be basic, e.g. in the range of 10 to 14, preferably about 12 to 14. A suitable inorganic base such as an alkaline earth hydroxide, e.g. sodium hydroxide, is useful. The reaction temperature will range from about 0° C. to about 60° C., preferably about 20° C. to about 25° C. The time needed for the reaction to be complete will generally be no more than 10 hours, preferably no more than about 4 hours. The mixture is then acidified to a pH of less than 4, e.g. 3, with an appropriate acid such as hydrochloric acid and extracted, if needed, with a suitable solvent such as ethyl acetate in accordance with standard chemical synthetic methods. Often the resulting propionic acid precipitates as a solid and is filtered off.

In step 2', the compound of formula C (i.e. the aminopropionic acid) is converted into the corresponding acid halide by reacting with a halogenated agent such as $SOCl_2$, $PCl_3$, $POCl_3$, $PCl_5$, $PBr_3$, and the like under appropriate conditions.

In step 3 of the process a compound of formula (D) or (D') is reacted with CPT or a CPT analog in about equimolar amounts under conditions suitable for the formation of the compounds of this invention as the 20-(S) stereoisomer. The reaction takes place in the presence of suitable coupling agent such as a carbodiimide compound, e.g. disopropylcarbodiimide, but preferably 1-(3-dimethylaminopropyl)-3-ethyl carbodiimide hydrochloride (EDCI) and 4-(dimethylamino) pyridine (DMAP) in the presence of a suitable solvent, preferably a nonaqueous, nonpolar solvent. Examples of useful solvents in this step include halogenated alkanes, e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, usually less than about 10 hours. It should be noted that a compound of formula (I) wherein one of $R_2$-$R_6$ is $R_aR_bN(CH_2)$—C(O)O— along with R being $R_aR_bN(CH_2)_2$ is obtained by reacting a CPT analog where one of $R_2$-$R_6$ (particularly $R_4$) is a hydroxy. In this case, the compound (e.g. the 10 hydroxy CPT), is reacted with 2 molar equivalents of the aminopropionic acid to give the disubstituted CPT derivative.

An alternative process for preparing preferred compounds of this invention involve starting with a suitable anhydride and converting it to an imidopropionic acid, which is in turn reacted with CPT or a CPT analog to give a compound of the invention in accordance with Step 3 of the reaction sequence above. This anhydride conversion can be visualized as follows:

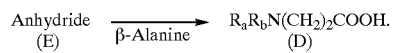

Generally the anhydride is reacted with β-alanine in the presence of a suitable solvent and a catalyst. Suitable solvents include polar, water-miscible solvents, such as alcohols, acetone, dioxane, and the like. Ethanol is preferred. A suitable catalyst is dimethylaminopyridine (DMAP). Generally, the reaction is carried out at reflux temperature for less than 10 hours, e.g. about three. Adding water results in the precipitation of the compound, which is then dried to give the resulting imidopropionic acid designated as (D). This compound is then reacted with CPT or a CPT analog to give a compound of this invention.

In step 1, of the reaction sequence above, suitable amines represented by formula (A) include the following:

1-(3-trifluoromethyl)phenylpiperazine;
1-(4-benzyl)piperazine;
1-[4-(3-methoxyphenyl)]piperazine;
1-[4-(4-nitrophenyl)]piperazine;
1-(4-phenyl)piperazine;
1-[4-(2-chlorophenyl)]piperazine (as the HCl salt);
1-[4-(4-fluorophenyl)]piperazine;
3-[4-(4-acetylphenyl)piperazine;
4-benzylpiperidine;
piperidine;
piperazine;
morpholine; and the like.

One of skill in the art will recognize other representative amines with the guidance of this specification.

In step 2, suitable 3-cyclicaminopropionic acid esters represented by formula (C) include the following:

ethyl 3-[4-(3-trifluoromethylphenyl)-1-piperazinyl]propionate;
ethyl 3-(4-benzyl-1-piperazinyl)propionate;
ethyl 3-[4-(4-nitrophenyl)-1-piperazinyl]propionate;
ethyl 3-(4-phenyl-1-piperazinyl)propionate;
ethyl 3-[4-(2-chlorophenyl)-1-piperazinyl]propionate;
ethyl 3-[4-(4-fluorophenyl)-1-piperazinyl]propionate;
ethyl 3-(4-benzyl-1-piperidino)propionate;
ethyl 3-[4-(4-acetylphenyl)-1-piperazinyl]propionate; and the like.

In step 3, a suitable CPT analog is a compound that is CPT substituted at the 7, 9, 10, 11, or 12 positions as described in this document. The CPT analog may be substituted with substituents known in the art or that can be prepared by one of skill in the art given the disclosure herein. Representative articles that teach how to make such analogs or where such analogs may be procured are found in the following journals (which are incorporated herein by reference):

1. *J. Med. Chem.* 1998, 41, 31–37
2. *J. Med. Chem.* 2000, 43, 3970–3980
3. *J. Med. Chem.* 1993, 36, 2689–2700
4. *J. Med. Chem.* 1991, 34, 98–107
5. *J. Med. Chem.* 2000, 43, 3963–3969
6. *Chem. Pharm. Bull.* 39(10) 2574–2580 (1991)
7. *Chem. Pharm. Bull.* 39(6) 1446–1454 (1991)
8. ANTIMICROBIAL AGENTS AND CHEMOTHERAPY, December 1999, p. 2862–2868
9. *European Journal of Cancer*, Vol. 34, No. 10, pp. 1500–1503, 1998
10. Cancer Research 55, 753–760, Feb. 15, 1995
11. *Anti-Cancer Drug Design* (1998), 13, 145–157
12. Bioorganic & Medicinal Chemistry Letters 8 (1998) 415–418
13. Cancer Research 61, 6034–6037, Aug. 15, 2001
14. Clinical Cancer Research, 7, 935–941, April 2001

Suitable CPT analogs include the following, where the number in parenthesis following the name refers to journal article listed above:

camptothecin (CPT);
(20S)-7-ethyl-10-[4-(1-piperidino)-1-piperidino]carbonyloxy)-CPT (AKA-irinotecan);
(20S)-9-nitro CPT (1);
(20S)-7-chloro-n-propyldimethylsilyl CPT (2);
(20S)-10-hydroxy-7-chloro-n-propyldimethylsilyl CPT (2);
(20S)-10-acetoxy-7-chloro-n-propyldimethylsilyl CPT (2);
(20S)-7-tert-butyldimethylsilyl CPT (2);
(20S)-10-hydroxy-7-tert-butyldimethylsilyl CPT (2);
(20S)-10-acetoxy-7-tert-butyldimethylsilyl CPT (2);
(20S)-9-hydroxy CPT (3);
(20S)-9-amino CPT (3);
(20S)-10-amino CPT (3);
(20S)-9-amino-10-hydroxy CPT (3);
(20S)-9-amino-10,11-methylenedioxy CPT (3);
(20S)-9-methylamino CPT;
(20S)-9-methyl CPT (3);
(20S)-9-dimethylamino CPT;
(20S)-9-chloro CPT (3);
(20S)-9-dimethylamino-10-hydroxy CPT (AKA topotecan);
(20S)-9-fluoro CPT (3);
(20S)-9-piperidino CPT;
(20S)-9-dimethylaminomethyl-10-hydroxy CPT (3);
(20S)-9-morpholinomethyl CPT (4);
(20S)-10-hydroxy CPT (3);
(20S)-9,10-dichloro CPT (3);
(20S)-10-bromo CPT (3);
(20S)-10-chloro CPT (3);
(20S)-10-methyl CPT (3);
(20S)-10-fluoro CPT (3);
(20S)-10-nitro CPT (3);
(20S)-10,11-methylenedioxy CPT (3);
(20S)-10-formyl CPT (3);
(20S)-10-nonylcarbonyloxy CPT (12);
(20S)-10-undecylcarbonyloxy CPT (12);
(20S)-10-pentadecylcarbonyloxy CPT (12);
(20S)-10-heptadecylcarbonyloxy CPT (12);
(20S)-10-nonadecylcarbonyloxy CPT (12);
(20S)-9-nitro-10,11-methylenedioxy CPT (3);
(20S)-9-(4-methylpiperazinylmethyl)-10-hydroxy (CPT) (4);
(20S)-9-[4-(1-piperidino)-1-piperidinomethyl]-10-hydroxy CPT (4);
(20S)-9-methyl-10,11-methylenedioxy CPT;
(20S)-9-chloro-10,11-methylenedioxy CPT (3);
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT (4);
(20S)-9-methylaminomethyl-10-hydroxy CPT;
(20S)-9-n-propylaminomethyl-10-hydroxy CPT (4);
(20S)-9-dimethylaminomethyl-10-hydroxy CPT (4);
(20S)-9-cyclohexylaminomethyl-10-hydroxy CPT (4);
(20S)-9-(2-hydroxyethyl)aminomethyl-10-hydroxy CPT (4);
(20S)-9-(trimethylammonio)methyl-10-hydroxy CPT, methanesulfonate (4);
(20S)-9-morpholinomethyl-10-hydroxy CPT (4);
(20S)-9-cyanomethyl-10-hydroxy CPT (4);
(20S)-9-trimethylsilylethylene CPT (14);
(20S)-CPT-7-aldehyde (5);
(20S)-10-methoxy CPT-7-aldehyde (5);
(20S)-7-(4-methylpiperazinomethylene)-10,11-ethylenedioxy CPT (14);
(20S)-7-butoxyimiomethyl CPT (13);
(20S)-7-acetoxymethyl CPT (5);
(20S)-7-acetoxymethyl-10-methyl CPT (5);
(20S)-7-cyano-10-methoxy CPT (5);
(20S)-7-cyano CPT (5);
(20S)-7-formylethenyl CPT (5);
(20S)-7-ethoxycarbonylethenyl CPT (5);
(20S)-7-cyanoethenyl CPT (5);
(20S)-7-(2,2-dicyanoethenyl) CPT (5);

(20S)-7-(2-cyano-2-ethoxycarbonyl)ethenyl CPT (5);
(20S)-7-ethoxycarbonylethyl CPT (5);
(20S)-7-ethyl CPT (6);
(20S)-7-n-propyl CPT (6);
(20S)-7-acetoxymethyl CPT (6);
(20S)-7-n-propylcarbonyloxymethyl CPT (6);
(20S)-7-ethoxycarbonyl CPT (6);
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocarbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4-(1-piperidino)-piperidino carbonyloxy CPT (7);
(20S)-7-ethyl-10-(1-piperazine) carbonyloxy CPT (7);
(20S)-7-ethyl-10-(4-i-propylaminocarbonylmethylpiperazine) carbonyloxy CPT (7);
(20S)-7-ethyl-10-[4(1-pyrrolidinyl) piperazine] carbonyloxy CPT (7);
(20S)-7-ethyl-10-[(4-(dimethylamino)-1-piperidino] carbonyloxy CPT (7);
(20S)-7-ethyl-10-[4-(di-n-propylamino)-1-piperidino] carbonyloxy CPT (7);
(20S)-7-ethyl-10-[(4-(di-n-butylamino)-1-piperidino] carbonyloxy CPT (7);
(20S)-7-ethyl-10-[4-(1-pyrrolidino)-1-piperidino)] carbonyloxy CPT (7);
(20S)-7-ethyl-10-[4-(1-piperidino)-1-piperidino] carbonyloxy CPT (7);
(20S)-7-ethyl-10-[N-methyl-N-2-(dimethylamino) ethylamino]carbonyloxy CPT (7);
(20S)-7,9-(1-amino-n-propylenyl)-10-methyl-11 fluoro CPT (14); and the like.

It will be recognized by one of skill in the art that other similar compounds may be prepared by following the teachings set forth in the above articles and modifying with appropriate art-recognized steps.

In step 3, suitable 3-aminopionic acids of formula (D) including the following:
3-phthalimidopropionic acid;
3-maleimidopropionic acid;
3-(3-nitro 1,8-naphthalimide)propionic acid;
3-(4-nito-1,8-naphthalimide)propionic acid;
3-(4-bromo-1,8-naphthalimido)propionic acid;
3-[4-(3-trifluoromethylphenyl)-1-piperazinyl]-propionic acid;
3-[(4-benzyl)-1-piperazinyl]propionic acid;
3-[4-(3-methoxyphenyl)-1-piperazinyl]propionic acid;
3-[4-(4-nitrophenyl)-1-piperazinyl]propionic acid;
3-(4-phenyl-1-piperazinyl)propionic acid;
3-[4-(2-chlorophenyl)-1-piperazinyl]propionic acid;
3-[4-(4-fluorophenyrl)-1-piperazinyl]propionic acid;
3-(1-piperidino)propionic acid;
3-[1-(4-benzyl)piperidino]propionic acid;
3-[4-(4-acetylphenyl-1-piperazinyl]propionic acid;
3-[4-(3,4-dichlorophenyl)-1-piperazinyl]propionic acid;
3-[4-(3,4-methylenedioxyphenyl)-1-piperazinyl] propionic acid;
3-[4-(4-chlorophenyl)-1-piperidinyl]propionic acid;
3-(4-formyl-1-piperazinyl)propionic acid;
3-(4-ethyl-1-piperazinyl)propionic acid;
3-[4-(4-chlorophenyl)phenylmethyl-1-piperazinyl] propionic acid;
3-(4-cyano-4-phenyl-1-piperidinyl) propionic acid;
3-trans-4-cinnamyl-1-piperazinyl) propionic acid;
3-[4-(2-methylphenyl)-1-piperazinyl] propionic acid;
3-[4-(2,3-dimethylphenyl)-1-piperazinyl] propionic acid;
3-[4-(1-piperidino)-1-piperidino]propionic acid;
3-[4-(2-pyrimidinyl)-1-piperazinyl] propionic acid;
3-(4-cyclohexyl-1-piperazinyl) propionic acid;
3-[4-(α-(2-pyridyl)benzyl-1-piperazinyl] propionic acid;
3-(4-morpholino)propionic acid;
3-(1-pyrrolinyl)propionic acid;
4-[4-(3-trifluoromethylphenyl)-1-piperazinyl] butyric acid;
5-[4-(3-trifluoromethylphenyl)-1-piperazinly] valeric acid; and the like.

One of skill in the art will recognize that other similar 3-aminopropionic acids may be obtained from commercial sources or prepared by art-recognized procedures to be used in step 3 to prepare compounds of this invention. By reacting a compound shown in the list of CPT analogs with a compound shown in the list of compounds of formula (D) in accordance with the guidelines for reaction condition, compounds of the invention will be obtained. These compounds will exhibit the desired charcteristics to a greater or lesser extent. Guidance is provided herein as to the preferred subgroups of compounds within the family.

EXAMPLES

The following examples are given to provide representative compounds included as part of this invention. The examples also provide descriptions of in vitro and in vivo assays to aid in determining the utility of the compounds. The camptothecin esters in examples 1–15 were prepared by the corresponding aminopropionic acid and camptothecin. Throughout the examples chemical formulas will be used to name compounds (e.g. $NaHCO_3$ is sodium bicarbonate) as appropriate. In naming the compounds, generally two approaches are used. One approach used in the section heading of each example is to refer to the compound as the camptothecin 20S-ester of the propionic acid. The other approach used is to refer to the compound as the camptothecin-20-O-3-propionate. Each approach is meant to name the same compound. E.g., in Example 1, the camptothecin-20S-ester of 3-phthalimidopropionic acid is the same compound as camptothecin-20-O-3-phthalimidopropionate.

Example 1

This example explains how to prepare non-substituted and substituted camptothecin-20S-esters of 2-phthalimidopropionic acid.

A. Camptothecin-20S-ester of 3-phthalimidopropionic acid (000503)

The mixture of camptothecin (10 mg, 0.029 mmol), 3-phthalimidopropionic acid (12.7 mg, 0.058 mmol), EDCl (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 12 mg camptothecin-20-O-3-phthalimidopropionate, mp 158–161° C.

The chemical structure analysis was performed by $^1$HNMR (CDCl$_3$, 600 MHz): δ 8.39 (s, 1H, Ar—H), 8.23 (d, 1H, Ar—H), 7.95 (d, 1H, Ar—H), 7.84 (t, 1H, Ar—H), 7.80 (s, 2H), Ar—H), 7.69 (t, 1H, Ar—H), 7.63 (s, 2H, Ar—H), 7.24 (s, 1H, Ar—H), 5.67 (d, 1H, H17), 5.40 (d, 1H, H17), 5.28 (s, 2H, H5), 4.00 (t, 2H, NCH$_2$), 2.98 (m, 2H, COCH$_2$), 2.25 (d, 2H, CH$_2$), 0.97 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 2

This example explains how to prepare non-substituted and substituted camptothecin-20S-esters of 3-maleimidopropionic acid.

A. Camptothecin-20S-ester of 3-maleimidopropionic acid (010104)

The mixture of camptothecin (10 mg, 0.029 mmol), 3-maleimidopropionic acid (10 mg, 0.059 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 6 mg cainptothecin-20-O-3-maleimidopropionate, mp 243–245° C.

The chemical structure analysis was performed by $^1$HNMR (CDCl$_3$, 600 MHz): δ 8.40 (s, 1H, Ar—H), 8.24 (d, 1H, Ar—H), 7.96 (d, 1H, Ar—H), 7.85 (t, 1H, Ar—H), 7.68 (t, 1H, Ar—H), 7.26 (s, 1H, Ar—H), 7.18 (s, 1H, Ar—H), 6.67 (s, 1H, Ar—H), 5.65 (d, 1H, H17), 5.41 (d, 1H, H17), 5.30 (s, 2H, H5), 3.84 (t, 2H, NCH$_2$), 2.93 (m, 2H, COCH$_2$), 2.25 (d, 2H, CH$_2$), 0.97 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-1-fluoro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;

7-methyl-10-aminocarbonyloxy CPT;
7-n-propyl-10-piperidinocarbonyloxy CPT;
7-ethyl-10-(2-dimethylamino)ethyl CPT; and the like.

Example 3

This example explains how to prepare non-substituted and substituted camptothecin-20S-esters of 3-(3-nitro-1,8-naphthalimide)propionic acid.

A. Camptothecin-20S-ester of 3-(3-nitro-1,8-naphthalimide) propionic acid (001117)

1. Synthesis of 3-(3-nitro-1,8-naphthalimide)propionic acid

The reaction mixture of 3-nitro-1,8-naphthalic anhydride (243 mg, 1.0 mol), β-alanine (90 mg, 1.0 mol), DMAP (10 mg, 0.1 mmol) and ethanol (15 ml) was refluxed for 3 h. Then 15 ml of water was added. The mixture was filtered, and the solid was washed with water, and then dried in the oven to give 224 mg 3-(3-nitro-1,8-naphthalimide)propionic acid as a gray solid, mp 250–255° C.

The chemical structure analysis was performed by $^1$HNMR (DMSO-$d_6$, 600 MHz): δ 9.39 (d, 1H, Ar—H), 8.85 (d, 1H, Ar—H), 8.70 (d, 1H, Ar—H), 8.61 (d, 1H, Ar—H), 8.00 (t, 1H, Ar—H), 4.25 (t, 2H, NCH$_2$), 2.62 (t, 2H, COCH$_2$).

2. Synthesis of camptothecin-20-0-[3-(3-nitro-1,8-naphthalimide)propionate]

A mixture of camptothecin (10 mg, 0.027 mmol), 3-(3-nitro-1,8-naphthalimide)-propionic acid (18 mg, 0.058 mmol), EDCI (25 mg, 0.13 mmol), DMAP (2 mg, 0.02 mmol), and dichloromethane (3 ml) were stirred at room temperature for 20 h, then dichloromethane (20 ml) was added to the solution. The organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH; 9:1) to afford 12 mg of the title compound, mp 225–227° C.

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;

9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 4

This example explains how to prepare non-substituted and substituted camptothecin-20S-esters of 3-(4-nitro-1,8-naphthalimide)propionic acid.

A. Camptothecin-20S-ester of 3-(4-nitro-1,8-naphthalimide) propionic acid (001128)

1. Synthesis of 3-(4-nitro-1,8-naphthalimide)propionic acid

The reaction mixture of 4-nitro-1,8-naphthalic anhydride (243 mg, 1.0 mol), β-alanine(125 mg, 1.4 mol), DMAP (10 mg, 0.1 mmol) and ethanol (15 ml) was refluxed for 3 h. Then 15 ml of water was added. The mixture was filtered, and the solid was washed with water, and then dried in the oven to give 227 mg 3-(4-nitro-1,8-naphtalimide)propionic acid as a gray solid, mp 220–222° C.

The chemical structure analysis was performed by $^1$HNMR (DMSO-$d_6$, 600 MHz): δ 8.69 (t, 1H, Ar—H), 8.60 (m, 2H, Ar—H), 8.54 (d, 1H, Ar—H), 8.08 (t, 1H, Ar—H), 4.25 (t, 2H, NCH$_2$), 2.62 (t, 2H, COCH$_2$).

2. Synthesis of camptothecin-20-O-[3-(4-nitro-1,8-naphthalimide)propionate]

The mixture of camptothecin (10 mg, 0.029 mmol), 3-(4-nitro-1,8-naphthalimide)-propionic acid (13 mg, 0.041 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 10 mg camptothecin-20-O-[3-(4-nitro-1,8-naphthalimide)propionate], mp 263–265° C.

The chemical structure analysis was performed by $^1$HNMR (CDCl$_3$, 600 MHz): δ 8.76 (d, 1H, Ar—H), 8.69 (d, 1H, Ar—H), 8.63 (d, 1H, Ar—H), 8.40 (s, 1H, Ar—H), 8.24 (d, 1H, Ar—H), 8.18 (d, 1H, Ar—H), 7.96 (d, 1H, Ar—H), 7.89 (t, 1H, Ar—H), 7.84 (t, 1H, Ar—H), 7.69 (t, 1H, Ar—H), 7.27 (d, 1H, Ar—H), 5.65 (d, 1H, H17), 5.42 (d, 1H, H17), 5.28 (s, 2H, H5), 4.52 (t, 2H, NCH$_2$), 2.96 (dm, 2H, COCH$_2$), 2.25 (d, 2H, CH$_2$), 0.93 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl) aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 5

This example explains how to prepare non-substituted and substituted camptothecin-20S-ester of 3-(4-bromo-1,8-naphthalimide)propionic acid.

A. Camptothecin-20S-ester of 3-(4-bromo-1,8-naphthalimide)propionic acid (001220)

1. Synthesis of 3-(4-bromo-1,8-naphthalimide)propionic acid

The reaction mixture of 4-bromo-1,8-naphthalic anhydride (277 mg, 1.0 mol), β-alanine (120 mg, 1.3 mol), DMAP (10 mg, 0.1 mmol) and ethanol (15 ml) was refluxed for 4 h. The mixture was filtered, and the solid was washed with ethanol, and then dried in the oven to give 300 mg 3-(4-bromo-1,8-naphthalimide)propionic acid as a gray solid, mp 220–225° C.

The chemical structure analysis was performed by $^1$HNMR (DMSO-$d_6$, 600 MHz): δ 8.58 (t, 2H, Ar—H), 8.35 (d, 1H, Ar—H), 8.24 (d, 1H, Ar—H), 8.01 (t, 1H, Ar—H), 4.25 (t, 2H, NCH$_2$), 2.59 (t, 2H, COCH$_2$).

2. Synthesis of camptothecin-20-O-[3-(4-bromo-1,8-naphthalimide) propionate]

The mixture of camptothecin (10 mg, 0.029 mmol), 3-(4-bromo-1,8-naphthalimide) propionic acid (19 mg, 0.056 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 12.3 mg camptothecin-20-O-[3-(4-bromo-1,8-naphthalimide)propionate], mp 250–252° C.(dec).

The chemical structure analysis was performed by $^1$HNMR (CDCl$_3$, 600 MHz): δ 8.61 (d, 1H, Ar—H), 8.49 (d, 1H, Ar—H), 8.38 (s, 1H, Ar—H), 8.36 (d, 1H, Ar—H), 8.19 (d, 1H, Ar—H), 7.94 (m, 2H, Ar—H), 7.84 (t, 1H, Ar—H), 7.75 (t, 1H, Ar—H), 7.68 (t, 1H, Ar—H), 7.29 (s, 1H, Ar—H), 5.65 (d, 1H, H17), 5.43 (d, 1H, H17), 5.28 (s, 2H, H5), 4.50 (t, 2H, NCH$_2$), 3.00 (dm, 2H, COCH$_2$), 2.25 (d, 2H, CH$_2$), 0.94 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-acetyloxy-10,11-methylenedioxy CPT;
9-acetylamino-10,11-methylenedioxy CPT;
9-aminomethyl-10-hydroxy CPT;
9-methylaminomethyl-1-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 6

This example explains how to prepare non-substituted and substituted camptothecia-20S-esters of 3-[4-(3-trifluoromethylphenyl)-1-piperazinyl]propionic acid.

A. Camptothecin-20S-ester of 3-[4-(3-trifluoromethylphenyl)-1-piperazinyl]-propionic acid (001101)

1. Synthesis of 3-[4-(3-trifluoromethylphenyl)-1-piperazinyl]propionic acid

The reaction mixture of 1-(3-trifluoromethylphenyl) piperazine (510 mg, 2.2 mmol), ethyl 3-bromopropionate (500 mg, 2.7 mmol), sodium bicarbonate (300 mg, 3.5 mmol) and ethanol (15 ml) was refluxed for 3 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 500 mg 3-[4-(3-trifluoromethylphenyl)-1-piperazinyl]propionic acid as a white solid, mp 228–230° C.

The chemical structure analysis was performed by $^1$HNMR (DMSO-$d_6$, 600 MHz): δ 7.47 (t, 1H, Ar—H), 7.29 (t, 2H, Ar—H), 7.15 (d, 1H, Ar—H), 3.36 (m, 10H, $NCH_2$), 2.89 (t, 2H, $COCH_2$).

2. Synthesis of camptothecin-20-O-3-[4-(3-trifluoromethylphenyl)-1-piperazinyl]propionate The mixture of camptothecin (10 mg, 0.029 mmol), 3-[4-(3-trifluoromethylphenyl)-1-piperazinyl]propionic acid (19 mg, 0.063 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3$: $CH_3OH$ 9:1) to afford 11.4 mg camptothecin-20-O-3-[4-(3-trifluoromethylphenyl)-1-piperazinyl]propionate, mp 87–90° C.

The chemical structure analysis was performed by $^1$HNMR (CDCl$_3$, 600 MHz): δ 8.35 (s, 1H, Ar—H), 7.99 (d, 1H, Ar—H), 7.89 (d, 1H, Ar—H), 7.64 (dt, 2H, Ar—H), 7.30 (s, 1H, Ar—H), 7.17 (t, 1H, Ar—H), 6.99 (d, 1H, Ar—H), 6.93 (s, 1H, Ar—H), 6.85 (d, 1H, Ar—H), 5.69 (d, 1H, H17), 5.42 (d, 1H, $H_{17}$), 5.28 (s, 2H, H5), 3.22 (m, 6H, $NCH_2$), 2.71 (m, 6H, $NCH_2$ and $COCH_2$), 2.25 (d, 2H, $CH_2$), 0.99 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 7

This example explains how to prepare non-substituted and substituted camptothecin-20S-esters of 3-[(4-benzyl)piperazin-1-yl]propionic acid.

A. Camptothecin-20S-ester of 3-[(4-benzyl)-1-piperazinyl]propionic acid (001204)

1. Synthesis of 3-[(4-benzyl)-1-piperazinyl]propionic acid

The reaction mixture 1-(4-benzyl)piperazine (380 mg, 2.16 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 265 mg 3-[(4-benzyl)-1-piperazinyl]propionic acid, mp 165–166° C.

The chemical structure analysis was performed by $^1$HNMR (DMSO-$d_6$, 600 MHz): δ 7.38 (m, 4H, Ar—H), 3.40–2.60 (m, 14H, $NCH_2$ and $COCH_2$).

2. Synthesis of camptothecin-20-O-3-[(4-benzyl)-1-piperazinyl]propionate

The mixture of camptothecin (10 mg, 0.029 mmol), 3-[(4-benzyl)piperazin-1-yl]propionic acid (14.3 mg, 0.058 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3$: $CH_3OH$ 9:1) to afford 8 mg camptothecin-20-O-3-[(4-benzyl)-1-piperazinyl]propionate, mp 206–208° C.(dec).

The chemical structure analysis was performed by $^1$HNMR (CDCl$_3$, 600 MHz): δ 8.40 (s, 1H, Ar—H), 8.20 (d, 1H, Ar—H), 7.95 (d, 1H, Ar—H), 7.83 (t, 1H, Ar—H), 7.68 (t, 1H, Ar—H), 7.23 (m, 6H, Ar—H), 5.67 (d, 1H, H17), 5.42 (d, 1H, H17), 5.29 (q, 2H, H5), 3.40 (s, 2H, NCH$_2$Ar), 2.73 (d, 4H, NCH$_2$CH$_2$CO), 2.52 (bs, 8H, NCH$_2$), 2.25 (d, 2H, CH$_2$), 0.98 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-dimethylaminomethyl-10-hydroxy CPT;
9-(2-hydroxyethyl) aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 8

This example explains how to prepare non-substituted and substituted camptothecin-20S-esters of 3-[4-(3-methoxyphenyl)-1-piperazinyl]propionic acid.
A. Camptothecin-20S-ester of 3-[4-(3-methoxyphenyl)-1-piperazinyl]propionic acid (001129)
1. Synthesis of 3-[4-(3-methoxyphenyl)-1-piperazinyl] propionic acid The reaction mixture 1-(4-(3-methoxyphenyl))piperazine (384 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 191 mg 3-[4-(3-methoxyphenyl)-1-piperazinyl]propionic acid, mp 180–183° C.

The chemical structure analysis was performed by $^1$HNMR (DMSO-d$_6$, 600 MHz): δ 10.75 (bs, 1H, COOH), 7.15 (t, 1H, Ar—H), 6.58 (d, 1H, Ar—H), 6.53 (s, 1H, Ar—H), 6.44 (d, 1H, Ar—H), 4.00–3.00 (m, 10H, NCH$_2$), 2.88 (t, 2H, COCH$_2$).

2. Synthesis of camptothecin-20-O-3-[4-(3-methoxyphenyl)-1-piperazinyl]propionate The mixture of camptothecin (10 mg, 0.029 mmol), 3-[4-(3-methoxyphenyl)-1-piperazin-1-yl]propionic acid (15.3 mg, 0.058 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 16 mg camptothecin-20-O-3-[4-(3-methoxyphenyl)-1-piperazin-1-yl]propionate, mp 98–100° C.

The chemical structure analysis was performed by $^1$HNMR (CDCl$_3$, 600 MHz): δ 8.35 (s, 1H, Ar—H), 8.06 (d, 1H, Ar—H), 7.91 (d, 1H, Ar—H), 7.71 (t, 1H, Ar—H), 7.64 (t, 1H, Ar—H), 7.31 (s, 1H, Ar—H), 7.05 (t, 1H, Ar—H), 6,60–6.30 (m, 3H, Ar—H), 5.68 (d, 1H, H17), 5.41 (d, 1H, H17), 5.28 (q, 2H, H5), 3.79 (s, 2H, NCH$_2$), 3.73 (s, 3H, OCH$_3$), 3.20 (t, 4H, NCH$_2$), 2.80–2.60 (m, 6H, NCH$_2$, CH$_2$CO), 2.25 (dm, 2H, CH$_2$), 1.00 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;

9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-dimethylaminomethyl-10-hydroxy CPT;
9-(2-hydroxyethyl) aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 9

This example explains how to prepare non-substituted and substituted camptothecin-20S-esters of 3-[4-(4-nitrophenyl)-1-piperazinyl]propionic acid.

A. Camptothecin-20S-ester of 3-[4-(4-nitrophenyl)-1-piperazinyl]propionic acid (010105)

1. Synthesis of 3-[4-(4-nitrophenyl)-1-piperazinyl]propionic acid

The reaction mixture 1-[4-(4-nitrophenyl)]piperazine (414 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 300 mg 3-[4-(4-nitrophenyl)-1-piperazinyl]propionic acid, mp 250–252° C.

The chemical structure analysis was performed by $^1$HNMR (DMSO-$d_6$, 600 MHz): δ 11.90 (bs, 1H, COOH), 8.11 (d, 2H, Ar—H), 7.14 (d, 2H, Ar—H), 3.34 (t, 1H, NCH$_2$), 2.88 (t, 2H, COCH$_2$).

2. Synthesis of camptothecin-20-O-3-[4-(4-nitrophenyl)-1-piperazinyl]propionate

The mixture of camptothecin (10 mg, 0.029 mmol), 3-[4-(4-nitrophenyl)-1-piperazinyl]propionic acid (16 mg, 0.058 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to 9.4 afford mg camptothecin-20-O-3-[4-(4-nitrophenyl)-1-piperazinyl]propionate, mp 255–257° C.(dec).

The chemical structure analysis was performed by $^1$HNMR (CDCl$_3$, 600 MHz): δ 8.34 (s, 1H, Ar—H), 7.98 (d, 1H, Ar—H), 7.91 (d, 2H, Ar—H), 7.88 (d, 1H, Ar—H), 7.63 (m, 2H, Ar—H), 7.30 (s, 1H, Ar—H), 6.56 (d, 2H, Ar—H), 5.69 (d, 1H, H17), 5.43 (d, 1H, H17), 5.28 (q, 2H, H5), 3.39, 3.33 (d, 4H, NCH$_2$), 2.76–2.56 (t, 8H, NCH$_2$), 2.25 (dm, 2H, CH$_2$), 1.00 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino -10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 10

This example explains how to prepare non-substituted and substituted camptothecin-20S-esters of 3-(4-phenyl-1-piperazinyl)propionic acid.

A. Camptothecin-20S-ester of 3-(4-phenyl-1-piperazinyl) propionic acid (010108)

1. Synthesis of 3-(4-phenyl-1-piperazinyl)propionic acid

The reaction mixture of 1-(4-phenyl)piperazine (324 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen-chloride. Solid was filtered and washed with water, and then dried to give 246 mg 3-(4-phenyl-1-piperazinyl)propionic acid, mp 213–215° C.

The chemical structure analysis was performed by ¹HNMR (DMSO-d₆, 600 MHz): δ 7.26 (t, 2H, Ar—H), 7.00 (d, 2H, Ar—H), 6.87 (t, 1H, Ar—H), 3.37 (t, 10H, NCH₂), 2.83 (t, 2H, COCH₂).

2. Synthesis of camptothecin-20-O-3-(4-phenyl-1-piperazinyl)propionate

The mixture of camptothecin (10 mg, 0.029 mmol), 3-(4-phenylpiperazin-1-yl)propionic acid (13.4 mg, 0.058 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO₃ aqueous solution (10 ml) and brine (20 ml), and then dried over MgSO₄. After the solvent was removed under reduced pressure, the resulting solid was separated by column chromatography (eluent: CHCl₃:CH₃OH 9.1) to 10.4 afford mg camptothecin-20-O-3-(4-phenyl-1-piperazinyl)propionate, mp 200–202° C.

The chemical structure analysis was performed by ¹HNMR (CDCl₃, 600 MHz): δ 8.34 (s, 1H, Ar—H), 7.98 (d, 1H, Ar—H), 7.91 (d, 2H, Ar—H), 7.88 (d, 1H, Ar—H), 7.63 (m, 2H, Ar—H), 7.30 (s, 1H, Ar—H), 6.56 (d, 2H, Ar—H), 5.69 (d, 1H, H17), 5.43 (d, 1H, H17), 5.28 (q, 2H, 1H5), 3.39, 3.33 (d, 4H, NCH₂), 2.76–2.56 (t, 8H, NCH₂), 2.25 (dm, 2H, CH₂), 2.83 (t, 2H, CH₃).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino -10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 11

This example explains how to prepare non-substituted and substituted camptothecin-20S-esters of 3-[4-(2-chlorophenyl)-1-piperazinyl]propionic acid.

A. Camptothecin-20S-ester of 3-[4-(2-chlorophenyl)-1-piperazinyl]propionic acid (010117)

1. Synthesis of 3-[4-(2-chlorophenyl)-1-piperazinyl] propionic acid

The reaction mixture 1-[4-(2-chlorophenyl)]piperazine monohydrochloride (466 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 246 mg 3-[4-(2-chlorophenyl)-1-piperazinyl]propionic acid, mp 210–213° C.

The chemical structure analysis was performed by ¹HNMR (D₂O, 600 MHz): δ 7.44 (d, 1H, Ar—H), 7.29 (t, 1H, Ar—H), 7.18 (d, 1H, Ar—H), 7.10 (t, 1H, Ar—H), 3.64–3.08 (m, 10H, NCH₂), 2.85 (t, 2H, COCH₂).

2. Synthesis of camptothecin-20-O-3-[4-(2-chlorophenyl)-1-piperazinyl]propionate The mixture of camptothecin (10 mg, 0.029 mmol), 3-[4-(2-chlorophenyl)-1-piperazinyl]propionic acid (15 mg, 0.056 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO₃ aqueous solution (10 ml) and brine (20 ml), and then dried over MgSO₄. After the solvent was removed under reduced pressure, the resulting solid was separated by column chromatography (eluent: CHCl₃:CH₃OH 9:1) to 14 afford mg camptothecin-20-O-3-[4-(2-chlorophenyl)-1-piperazinyl]propionate, mp 190–192° C.

The chemical structure analysis was performed by ¹HNMR (CDCl₃, 600 MHz): δ 8.38 (s, 1H, Ar—H), 8.07 (d, 1H, Ar—H), 7.91 (d, 1H, Ar—H), 7.71 (t, 1H, Ar—H), 7.64 (t, 1H, Ar—H), 7.30 (s, 1H, Ar—H), 7.28 (d, 1H, Ar—H), 6.98 (t, 1H, Ar—H), 6.88 (t, 1H, Ar—H), 6.70 (d, 1H, Ar—H), 5.68 (d, 1H, H17), 5.42 (d, 1H, H17), 5.28 (q, 2H, H5), 3.06 (s, 4H, NCH₂), 2.76–2.56 (t, 8H, NCH₂), 2.25 (dm, 2H, CH₂), 1.00 (t, 3H, CH₃).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;

9-dimethylamino CPT;

9-dimethylaminomethyl-10-hydroxy CPT (AKA topotecan);

9-piperidino CPT;

9-morpholino CPT 7-ethyl-10-[4-(1-piperidino)-1-piperidino]carbonyloxy)-CPT (AKA irinotecan);

7-t-butyldimethylsilyl CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,11-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-trimethylsilylethylene CPT;

7-(4-methylpiperazinomethylene)-10,11-ethylenedioxy CPT;

7-butoxyiminomethyl CPT;

7,9-(1-amino-n-propylenyl)-10-methyl-11-fluoro CPT;

9-morpholinomethyl-10-hydroxy CPT;

7-ethyl-10-hydroxy CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example 12

This example explains how to prepare non-substituted and substituted camptothecin-20S-esters of 3-[4-(4-fluorophenyl)-1-piperazinyl]propionic acid.

A. Camptothecin-20S-ester of 3-[4-(4-fluorophenyl)-1-piperazinyl]propionic acid (010124)

1. Synthesis of 3-[4-(4-fluorophenyl)-1-piperazinyl] propionic acid

The reaction mixture 1-[4-(4-fluorophenyl)]piperazine (360 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 482 mg 3-[4-(4-fluorophenyl)-1-piperazinyl]propionic acid, mp 178–180° C.

The chemical structure analysis was performed by $^1$HNMR (DMSO-$d_6$, 600 MHz): δ 7.09 (d, 2H, Ar—H), 7.04 (t, 2H, Ar—H), 3.40–3.32 (m, 1H, NCH$_2$), 2.91 (t, 2H, COCH$_2$).

2. Synthesis of camptothecin-20-O-3-[4-(4-fluorophenyl)-1-piperazinyl]-propionate The mixture of camptothecin (10 mg, 0.029 mmol), 3-[4-(4-fluorophenyl)-1-piperazinyl]propionic acid (15 mg, 0.056 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 12 mg camptothecin-20-O-3-[4-(4-fluorophenyl)-1-piperazinyl]propionate, mp 162–165° C.

The chemical structure analysis was performed by $^1$HNMR (CDCl$_3$, 600 MHz): δ 8.36 (s, 1H, Ar—H), 8.05 (d, 1H, Ar—H), 7.92 (d, 2H, Ar—H), 7.72 (t, 1H, Ar—H), 7.65 (t, 2H, Ar—H), 7.28 (s, 1H, Ar—H), 6.79 (m, 2H, Ar—H), 6.65 (m, 2H, Ar—H), 5.71 (d, 1H, H17), 5.43 (d, 1H H17), 5.27 (q, 2H, H5), 3.11 (t, 4H, NCH$_2$), 2.83–2.50 (m, 8H, CH$_2$), 2.25 (dm, 2H, CH$_2$), 0.98 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;

9-nitro CPT;

9-amino CPT;

9-amino -10-hydroxy CPT;

9-methylamino CPT;

9-dimethylamino CPT;

9-dimethylaminomethyl-10-hydroxy CPT (AKA topotecan);

9-piperidino CPT;

9-morpholino CPT 7-ethyl-10-[4-(1-piperidino)-1-piperidino]carbonyloxy)-CPT (AKA irinotecan);

7-t-butyldimethylsilyl CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,11-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-morpholinomethyl-10-hydroxy CPT;

7-ethyl-10-hydroxy CPT;

9-trimethylsilylethylene CPT;

7-(4-methylpiperazinomethylene)-10,11-ethylenedioxy CPT;

7-butoxyiminomethyl CPT;

7,9-(1-amino-n-propylenyl)-10-methyl-11-fluoro CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example 13

This example explains how to prepare non-substituted and substituted camptothecin-20-O-3-(1-piperidino)propionates.

A. Camptothecin-20-O-3(1-piperidino)propionate (001124)

The mixture of camptothecin (10 mg, 0.029 mmol), 3-(1-piperidino)propionic acid (10 mg, 0.063 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 5 mg camptothecin-20-O-3(1-piperidino)propionate, mp 175–177° C.

The chemical structure analysis was performed by $^1$HNMR (CDCl$_3$, 600 MHz): δ 8.39 (s, 1H, Ar—H), 8.20 (d, 1H, Ar—H), 7.94 (d, 1H, Ar—H), 7.83 (t, 1H, Ar—H), 7.67 (t, 1H, Ar—H), 7.26 (s, 1H, Ar—H), 5.70 (d, 1H, H17), 5.41 (d, 1H, H17), 5.29 (s, 2H, H5), 2.79 (d, 4H, NCH$_2$), 2.52 (bs, 4H, NCH$_2$CH$_2$CO), 2.25 (d, 2H, H118), 1.62 (6H, CH$_2$), 1.00 (s, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-trimethylsilylethylene CPT;
7-(4-methylpiperazinomethylene)-10,11-ethylenedioxy CPT;
7-butoxyiminomethyl CPT;
7,9-(1-amino-n-propylenyl)-10-methyl-11-fluoro CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 14

This example explains how to prepare non-substituted and substituted camptothecin-20S-esters of 3-[1-(4-benzyl)piperidino]propionate.

A. Camptothecin-20S-ester of 3-[1-(4-benzyl)piperidino]propionate (010122)

1. Synthesis of 3-[1-(4-benzyl)piperidino]propionic acid

The reaction mixture of 4-benzylpiperidine (350 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrochloric acid. Solid was filtered and washed with water, and then dried to give 346 mg, 3-[1-(4-benzyl)piperidino]propionic acid, mp 214–215° C.

The chemical structure analysis was performed by $^1$HNMR (DMSO-d$_6$, 600 MHz): δ 7.29 (t, 2H, Ar—H), 7.19 (m, 3H, Ar—H), 3.40 (d, 2H, NCH$_2$), 3.22 (d, 4H, CH$_2$), 2.86 (m, 5H, CH$_2$CH$_2$CO and H4), 2.56 (s, 2H, Ar—CH$_2$), 1.74 (m, 5H, CH$_2$).

2. Synthesis of camptothecin-20-O-3-[1-(4-benzyl)piperidino]propionate

The mixture of camptothecin (10 mg, 0.029 mmol), 3-[1-(4-benzyl)piperidino]propionic acid (14 mg, 0.056 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 10 mg camptothecin-20-O-3-[1-(4-benzyl)piperidino]propionate, mp 195–197° C.

The chemical structure analysis was performed by $^1$HNMR (CDCl$_3$, 600 MHz): δ 8.39 (s, 1H, Ar—H), 8.22 (d, 1H, Ar—H), 7.95 (d, 1H, Ar—H), 7.83 (t, 1H, Ar—H), 7.67 (t, 1H, Ar—H), 7.22 (m, 3H, Ar—H), 7.15 (d, 1H, Ar—H), 7.04 (d, 2H, Ar—H), 5.69 (d, 1H, H17), 5.42 (d, 1H, H17), 5.29 (q, 2H, H5), 2.90 (d, 2H, NCH$_2$), 2.79 (d, 4H, NCH$_2$), 2.42 (d, 2H, Ar—CH$_2$), 2.25 (dm, 2H, CH$_2$), 1.94–1.20 (m, 5H, CH$_2$CHCH$_2$), 1.00 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT 7-ethyl-10-[4-(1-piperidino)-1-piperidino]carbonyloxy)-CPT (AKA irinotecan);

7-t-butyldimethylsilyl CPT;

9-trimethylsilylethylene CPT;

7-(4-methylpiperazinomethylene)-10,11-ethylenedioxy CPT;

7-butoxyiminomethyl CPT;

7,9-(1-amino-n-propylenyl)-10-methyl-11-fluoro CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,11-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-morpholinomethyl-10-hydroxy CPT;

7-ethyl-10-hydroxy CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example 15

This example explains how to prepare non-substituted and substituted camptothecin-20S-esters of 3-[4-(4-acetylphenyl)-1-piperazinyl]propionic acid.

A. Camptothecin-20S-ester of 3-[4-(4-acetylphenyl)-1-piperazinyl]propionic acid (010201)

1. Synthesis of 3-[4-(4-acetylphenyl)-1-piperazinyl]propionic acid

The reaction mixture 1-[4-(4-acetylphenyl)]piperazine (408 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 330 mg 3-[4-(4-acetylphenyl)-1-piperazinyl]propionic acid, mp 204–206° C.

The chemical structure analysis was performed by $^1$HNMR (DMSO-$d_6$, 600 MHz): δ 7.86 (d, 2H, Ar—H), 7.07 (d, 2H, Ar—H), 3.40–3.32 (m, 10H, NCH$_2$), 2.82 (t, 2H, COCH$_2$), 2.48 (s, 3H, COCH$_3$).

2. Synthesis of comptothecin-20-O-3-[4-(4-acetylphenyl)-1-piperazinyl]propionate The mixture of camptothecin (10 mg, 0.029 mmol), 3-[4-(4-acetylphenyl)-1-piperazinyl]propionic acid (16 mg, 0.058 mmol), EDCI (25 mg, 0.13 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$: CH$_3$OH 9:1) to afford 8.7 mg camptothecin-20-O-3-[4-(4-acetylphenyl)-1-piperazinyl]propionate, mp 218–220° C.(dec).

The chemical structure analysis was performed by $^1$HNMR (CDCl$_3$, 600 MHz): δ 8.34 (s, 1H, Ar—H), 8.02 (d, 1H, Ar—H), 7.88 (d, 1H, Ar—H), 7.72 (d, 2H, Ar—H), 7.62 (m, 2H, Ar—H), 7.31 (s, 1H, Ar—H), 6.66 (d, 2H, Ar—H), 5.69 (d, 1H, H17), 5.42 (d, 1H, H17), 5.28 (q, 2H, H5), 3.35 (d, 4H, NCH$_2$), 2.79–2.60 (t, 8H, NCH$_2$), 2.50 (s, 3H, COCH$_3$), 2.25 (dm, 2H, CH$_2$), 1.00 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;

9-nitro CPT;

9-amino CPT;

9-amino-10-hydroxy CPT;

9-methylamino CPT;

9-dimethylamino CPT;

9-dimethylaminomethyl-10-hydroxy CPT (AKA topotecan);

9-piperidino CPT;

9-morpholino CPT 7-ethyl-10-[4-(1-piperidino)-1-piperidino]carbonyloxy)-CPT (AKA irinotecan);

9-trimethylsilylethylene CPT;

7-(4-methylpiperazinomethylene)-10,11-ethylenedioxy CPT;

7-butoxyiminomethyl CPT;

7,9-(1-amino-n-propylenyl)-10-methyl-11-fluoro CPT;

7-t-butyldimethylsilyl CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,11-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-morpholinomethyl-10-hydroxy CPT;

7-ethyl-10-hydroxy CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example 16

This example provides directions for growing cells and testing compounds of the invention for their effect on the growth of the cells. All cells were purchased from DCTDC Tumor Repository, NCI, NIH.

Cell Colony Formation Assay

Four hundred cells (HCT 116, PC-3) or five hundred cells (VM46) were plated in 60 mm Petri dishes containing 2.7 ml of medium (modified McCoy's 5a medium) containing 10% fetal bovine serum and 100 units/ml penicillin and 100 mg/ml streptomycin. The cells were incubated in a $CO_2$ incubator at 37° C. for 5 hours for attachment to the bottom of Petri dishes. Drugs were made fresh in medium at ten times the final concentration, and then 0.3 ml of this stock solution was added to the 2.7 ml of medium in the dish. The cells were then incubated with drugs for 72 hours at 37° C. At the end of the incubation the drug-containing media were decanted, the dishes were rinsed with 4 ml of Hank's Balance Salt Solution (HBSS), 5 ml of fresh medium was added, and the dishes were returned to the incubator for colony formation. The cell colonies were counted using colony counter after incubation for 7 days for HCT 116 cells and PC-3 cells and 8 days for VM46 cells, respectively. Cell survival (%) was calculated, as shown in Table I for HCT 116 cells.

Values of ID50 (the drug concentration producing 50% inhibition of colony formation) may be determined for each tested compound. The directions described in this example may be used in other cells, such as DU-145.

TABLE I

This table provides results of in vitro efficacy tests performed in example 16 for the cell line HCT116.

| Compound | Survival (%) of HCT116 | | | |
| --- | --- | --- | --- | --- |
| (Example #) | 100 nM | 10 nM | 1 nM70.82 | MTD (mg/kg) |
| Camptothecin | 0 | 73.72 | | 12 |
| Irinotecan | 90.52 | | | |
| 000503 (1) | 0 | 95.24 | | 150 |
| 001117 (3) | 0 | 100 | | |
| 001128 (4) | 0 | 100 | | 150 |
| 010104 (2) | 0 | 95.54 | | |
| 001101 (6) | 0 | 0 | 100 | 150 |
| 001129 (8) | 0 | 0 | 73.26 | 150 |
| 001204 (7) | 0 | 0 | 64.04 | |
| 001124 (13) | 0 | 0 | 64.76 | |
| 010105 (9) | 0 | 0 | 94.14 | |
| 010108 (10) | 0 | 0 | 100 | |
| 010117 (11) | 0 | 0 | 100 | |
| 010122 (14) | 0 | 0 | 100 | |
| 010124 (12) | 0 | 0 | | |

Example 17

This example provides directions for performing in vivo toxicity tests of the compounds of the invention on C3H/HeJ mice.

Acute toxicities of the compounds of this invention are evaluated on C3H/HeJ mice (body weight 18–22 g). The MTD40 (maximum tolerated dose at day 40) values are determined by the standard procedure described by Gad and Chengelis (see, for example, "Acute Toxicology Testing," $2^{nd}$ Ed., Shayne O. Gad and Christopher P. Chengelis, pp. 186–195 (Academic Press).) In the consecutive type studies, 2 mice are dosed at low and moderate doses of 40 and 100 mg/kg. If no severe and irreversible toxicity (euthanasia is required) occurs at these doses, a new pair of animals is initiated at 180 mg/kg, which is 1.8 times higher than 100 mg/kg. Sequential dosages (about 3 doses on 3 pairs of animals, i.e. 2 mice for each drug dose) are increased by a factor of 1.8 until severe and irreversible toxicity (euthanasia is required) occurred. Then another pair of animals is initiated at the highest nonlethal dosage, and successive dosages were increased by a factor of 1.15. The result of this exercise is two dosages, one apparently nonlethal and the other lethal if severe and irreversible toxicity occurs and euthanasia is required, separated by a factor of 1.15. Six mice are dosed at each dosage. If no severe and irreversible toxicity occurs at the lower dosage and at least one with severe and irreversible toxicity occurs at the higher dose, then the lower dose is considered to be the MTD. The compounds of this invention are administered to C3H/HeJ mice by intraperitoneal injection. Drug toxicity is evaluated on mice checked daily for 45 days. The toxicity parameters reported will be the MTD40. The MTD is defined as the highest dose causing no severe irreversible toxicity in one treatment group, but at least one animal exhibiting severe and irreversible toxicity and being euthanized at the next higher dose.

Example 18

This example provides directions for performing in vivo efficacy tests of the compounds of the invention on C3H/HeJ mice bearing MTG-B tumors.

Studies on the compounds of this invention are performed on C3H/HeJ mice bearing MTG-B tumors. The tumors grow exponentially following implantation into the flanks of the mice and reached a diameter of 8 mm (268.08 $mm^3$) by day 7 to 10. Treatment is initiated at that time, with the first day of treatment designated as day 0 for calculation and plots. The mice are injected i.p. with three drug dose levels (1/3, 1/2, 1 5 MTD) using both a single injection and the schedule of Q2D 5 3 (every 2 days for a total of 3 treatments at 1/3 MTD). Control groups of mice bearing 8 mm diameter tumors are treated with vehicle alone. After drug treatment, the mice are observed twice a day. When a tumor reaches 1.5 g, the mouse bearing the tumor wis euthanized. Surviving days measured from day 0 for mice treated with anticancer drugs (T) and surviving days measured from day 0 for control mice (C) are recorded. Tumor growth inhibition values (T/C %) are calculated using the formula T/C %=(surviving days of mice treated with an anticancer drug T/surviving days of control mice C) 5 100%.

Tumor sizes may be measured by caliper every day. Daily measurement (mm) of solid tumor (length L and width W) in two dimensions is used to calculate the tumor weight [tumor weight=(length 5 $width^2$)/2] based on the interchangeable value of 1 $mm^3$=1 mg. Tumor growth delay (T–C value) is determined by calculation of the median time (in days) required for the treatment group and control group tumors to reach 1,000 mg. Tumor doubling time (Td) is measured, and tumor cell kill is calculated by the formula of log cell kill=(T–C value)/(3.32 5 Td). Regression effects after treatment may be observed and recorded (a complete regression: a regression below limit of palpation; a partial regression: a regression of more than 50% reduction in tumor mass).

Generally, the survival time of the control mice is six (6) days. A ratio of the extra days of survival of mice treated with the compounds of the invention (compared to control) to the extra days of survival of mice treated with taxol (compared to control), can be calculated. For example, if the mice survived 18 days as compared to 9 days for taxol-treated mice, the CD/Taxol ratio would be 18−6/9−6=12/3=4.

Example 19

This example provides guidance for determining the hydrolysis kinetics of the lactone ring (E) of camptothecin derivatives in the presence of different blood components. A quantitative $C_{18}$ reversed-phase high-performance liquid chromatography (HPLC) assay can be employed. A description is found at the following references:

*J. Med. Chem.* 2000, 43, 3970–3980;

*Anal. Biochem.* 1993, 212, 285–287; and

*Biochemistry* 1994, 33, 10325–10336.

See also *J. Med. Chem.* 1998, 41, 31–37.

Example 20

This example provides guidance for determining the inhibition of topoisomerase I. This procedure is an intact cell assay and is a modification of a published procedure found at *Cancer Res.* 1986, 46, 2021–2026. A more recent publication can be found at *J. Med. Chem.* 1993, 36 2689–2700 at 2699. Here the modification of the previous procedure was used to quantitate the amount of topoisomerase I mediated DNA cleavage in intact cells. The DNA of HL-60 cells growing in culture is labeled by [$^3$H] thymidine incorporation. The cells are exposed to compounds to be tested and lysed, and the protein is precipitated. Radioactive DNA in cleavable complex formation with topoisomerase I coprecipitates with the protein. The amount of cleavable complex formation is quantitated by counting the pellet with a liquid scintillation counter.

The subject matter claimed is:

1. A compound of the formula:

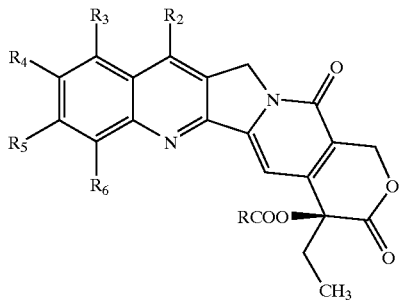

wherein R is $R_aR_bN$—$(CH_2)_m$, m is an integer from 1–10, and each of $R_a$ and $R_b$ is independently phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperidino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

lower alkoxy; or $R_aR_b$ together with N form a cyclic amine or imide ring; and $R_2$ is —$CH_2NR_7R_8$ (where $R_7$ and $R_8$ together with N are cyclic amino), butoxyiminomethyl, hydrogen, or together with $R_3$ is —$CH_2(NR_{12}R_{13})$—$CH_2$—$CH_2$— (where $R_{12}$ and $R_{13}$ each is independently hydrogen or lower alkyl);

$R_3$ is hydrogen, trialkylsilylethylene or together with $R_2$ is —$CH_2(NR_{12}R_{13})$—$CH_2$—$CH_2$— (where $R_{12}$ and $R_{13}$ each is independently hydrogen or lower alkyl);

$R_4$ is hydrogen, lower alkyl or together with $R_5$ is ethylenedioxy;

$R_5$ is hydrogen, halo or together with $R_4$ is ethylenedioxy; and $R_6$ is hydrogen, wherein:

if $R_2$ is —$CH_2NR_7R_8$ (where $R_7$ and $R_8$ taken together with —N— represent a cyclic amino) then $R_3$ and $R_6$ are H and $R_4$ and $R_5$ taken together represent ethylenedioxy;

if $R_2$ is butoxyiminomethyl then each of $R_3$, $R_4$, $R_5$ and $R_6$ is H;

if $R_2$ is hydrogen then $R_3$ is trialkylsilylethylene and each of $R_4$, $R_5$, and $R_6$ is H; and if $R_2$ and $R_3$ together represent —$CH(NR_{12}R_{13})$—$CH_2$—$CH_2$— then $R_4$ is lower alkyl, $R_5$ is halo, and $R_6$ is H, wherein $R_{12}$ and $R_{13}$ each is independently H or lower alkyl.

2. The compound of claim 1, wherein n is 2 and $R_aR_b$ taken together with N form a cyclic amine or imide ring.

3. The compound of claim 2, wherein $R_aR_b$ taken together with N form a six-membered cyclic amine.

4. The compound of claim 3, wherein the cyclic amine is piperazine optionally substituted at the 4-position with phenyl, substituted phenyl, benzyl, or substituted benzyl.

5. The compound of claim 4, wherein $R_2$ is —$CH_2NR_7R_8$ (where $R_7$ and $R_8$ taken together with —N— represent 4-methylpiperazinomethylene) when $R_3$ and $R_6$ are H and $R_4$ and $R_5$ taken together represent ethylenedioxy.

6. The compound of claim 4, wherein $R_2$ is butoxyiminomethyl when each of $R_3$, $R_4$, $R_5$ and $R_6$ is H.

7. The compound of claim 4, wherein $R_3$ is trimethylsilylethylene when each of $R_2$, $R_4$, $R_5$, and $R_6$ is H.

8. The compound of claim 4, wherein $R_2$ and $R_3$ together represent —$CH(NH_2)$—$CH_2$—$CH_2$— when $R_4$ is methyl, $R_5$ is fluoro, and $R_6$ is H.

9. The compound of claim 2, wherein $R_aR_b$ taken together with —N— form an imide ring.

10. The compound of claim 9, wherein $R_2$ is —$CH_2NR_7R_8$ (where $R_7$ and $R_8$ taken together with —N— represent 4-methylpiperazinomethylene) when $R_3$ and $R_6$ are H and $R_4$ and $R_5$ taken together represent ethylenedioxy.

11. The compound of claim 9, wherein $R_2$ is butoxyiminomethyl when each of $R_3$, $R_4$, $R_5$ and $R_6$ is H.

12. The compound of claim 9, wherein $R_3$ is trimethylsilylethylene when each of $R_2$, $R_4$, $R_5$, and $R_6$ is H.

13. The compound of claim 9, wherein $R_2$ and $R_3$ together represent —$CH(NH_2)$—$CH_2$—$CH_2$— when $R_4$ is methyl, $R_5$ is fluoro, and $R_6$ is H.

14. A pharmaceutical composition useful for treating colon or breast cancer in a warm-blooded animal, which composition comprises a compound as defined in claim 1 in combination with a pharmaceutically acceptable excipient.

15. The pharmaceutical composition of claim 14 suitable for oral administration.

16. The pharmaceutical composition of claim 14 suitable for IV administration.

17. The pharmaceutical composition of claim 14 suitable for IM administration.

18. A method for treating colon or breast cancer in a warm-blooded animal, which method comprises administering a therapeutically effective amount of a compound as defined in claim 1.

19. The method of claim 18, wherein the compound is administered orally.

20. The method of claim 18, wherein the compound is administered IV.

21. The method of claim 18, wherein the compound is administered parenterally.

22. A process of preparing a compound of claim 1, which comprises reacting
   (a) a compound of the formula R—C(O)X, wherein R is $R_aR_bN(CH_2)_2$ as defined as in claim 1, and X is hydroxy, chloride, or R—C(O)—O (where R is defined hereinbefore) with
   (b) a compound of the formula:

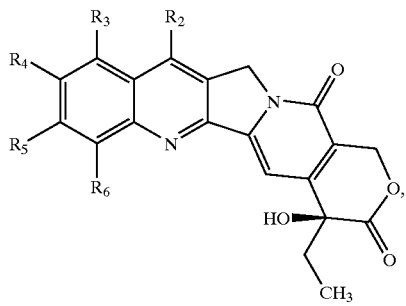

wherein $R_2$, $R_3$, $R_4$, $R_5$, and $R_6$ are defined in claim 1.

23. The process of claim 22 wherein the reacting takes place in the presence of the coupling agent, 1-(3-dimethylaminopropyl)-3-ethylcarbodiimide, hydrochloride, and the catalyst, 4-(dimethylamino) pyridine.

24. A pharmaceutical composition useful for treating colon or breast cancer in a warm-blooded animal, which composition comprises a compound as defined in claim 1, formulated for liposomal delivery.

25. The composition of claim 24, wherein n is 2 and $R_aR_b$ taken together with N form a cyclic amine or imide ring.

26. The composition of claim 25, wherein $R_aR_b$ taken together with N form a six-membered cyclic amine.

27. The composition of claim 25, wherein the cyclic amine is piperazine optionally substituted at the 4-position with phenyl, substituted phenyl, benzyl, or substituted benzyl.

28. The composition of claim 25, wherein $R_aR_b$ taken together with N form an imide ring.

29. A method for modulating topoisomerase comprising contacting a compound as defined in claim 1 with a topoisomerase I.

* * * * *